US00PP18465P2

(12) United States Plant Patent
Gutter

(10) Patent No.: US PP18,465 P2
(45) Date of Patent: Jan. 29, 2008

(54) ***AUBRIETA* PLANT NAMED 'AUDELMAG'**

(50) Latin Name: *Aubrieta hybrida*
Varietal Denomination: Audelmag

(75) Inventor: Martien Gutter, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/487,528

(22) Filed: Jul. 14, 2006

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

PBR 20051044—published Aug. 15, 2005.*
PBR 06–5688—filed Dec. 7, 2006.*

* cited by examiner

*Primary Examiner*—Wendy C. Haas
*Assistant Examiner*—Georgia Helmer
(74) *Attorney, Agent, or Firm*—Bruce Vrana

(57) ABSTRACT

A new *Aubrieta* plant, characterized particularly as to novelty by the early flowering, the grey green leaf color and the magenta flowers with white yellow heart.

1 Drawing Sheet

Latin name of the genus and species of the plant claimed: *Aubrieta hybrida.*
Varietal denomination: 'Audelmag'.

BACKGROUND OF THE NEW PLANT

The present invention comprises a new distinct cultivar of *Aubrieta,* botanically known as *Aubrieta hybrida.*

The new *Aubrieta* is a product of a planned breeding program conducted in Enkhuizen, Netherlands. The new *Aubrieta* cultivar has a compact growth habit and an early flowering in several colors.

The present cultivar originates from a proprietary *Aubrieta* selection identified as 'C0131,' not patented. A seedling from this selection was selected in 2002.

The present cultivar has been repeatedly asexually reproduced by cuttings in Enkhuizen, Netherlands, in Angers, France, in Gilroy, USA since 2002.

The distinctive characteristics of this new *Aubrieta* are stable and reproduced true to type in successive generations of asexual reproduction. It takes 25 to 29 weeks to produce a finished plant, depending on the temperature.

This new *Aubrieta* plant is a perennial in all climatic zones in the US.

DESCRIPTION OF THE DRAWING

This new *Aubrieta* plant is illustrated by the accompanying photographic drawing of a 28 week old plant which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new *Aubrieta.* The data which defines these characteristics were collected from asexual reproductions carried out in Enkhuizen, Netherlands. The plant history was taken on 35 week old plants, blossomed under natural light in the field.

Color readings were taken in the office under ambient light. Color references are primarily to The R.H.S. Colour Chart of The Royal Horticultural Society of London.

Plants of the new *Aubrieta* differ primarily from the plants of the parent selection in the following characteristics:

Plants of the new variety have magenta flowers and a compact growth habit, whereas plants of the parent selection have red flowers and a very loose growth habit.

TABLE 1

DIFFERENCES BETWEEN THE NEW CULTIVAR 'AUDELMAG' AND A SIMILAR CULTIVAR

| | 'Audelmag' | 'Red Carpet' (Not patented) |
|---|---|---|
| Earliness | Early | Late |
| Flower color | Big white eye | White eye absent or very small |

Parentage:
*Parent.*—'C0131,' not patented.
Propagation:
*Type cutting.*—Terminal cuttings.
*Time to initiate roots.*—12–14 days at 18° C.
*Time to produce a rooted cutting.*—5 weeks.
*Root description.*—Fine, fibrous and white in color.
Plant description:
*General appearance.*—Makes long branches that tend to grow decumbent.
*Growth and branching habit.*—Freely branching habit, freely flowering. Vigorous.
*Plant height.*—6 cm.
*Plant spread.*—28 cm.
Lateral branches:
*Length.*—Primary branch: 10–15 cm. Secondary branch: 4–8 cm.
*Diameter.*—0.15 cm.
*Texture.*—Smooth, pubescent.

*Internode length.*—0.5–3 cm.
*Colour.*—RHS 143C.

Foliage description:
*Arrangement.*—Alternate.
*Length, mature leaves.*—2 cm.
*Width, mature leaves.*—0.7 cm.
*Shape.*—Oblanceolate.
*Apex.*—Acute.
*Base.*—Attenuate.
*Margin.*—Dentate. Only two dents per leaf.
*Texture.*—Smooth, strongly pubescent.
*Venation pattern.*—Pinnate. Veins are hardly visible.
*Color young foliage, upper surface.*—RHS 138B.
*Color young foliage, lower surface.*—RHS 139C.
*Fully expanded foliage, upper surface.*—RHS 138B.
*Fully expanded foliage, lower surface.*—RHS 139C.
*Venation, upper surface.*—RHS 142B.
*Venation, lower surface.*—RHS 142B.
*Petiole.*—Absent.

Flower description:
*Flower type.*—Single, cruciform.
*Number of flowers and flower buds per lateral branch.*—1–5.
*Flower position.*—At top of branch.
*Fragrance.*—Absent.
*Flowering season.*—Spring.
*Flower diameter.*—1.5–2 cm.

Flower buds:
*Bud length* (*at stage of showing color*).—0.7 cm.
*Bud diameter.*—0.4 cm.
*Bud shape.*—Ovate.
*Texture.*—Smooth, pubescent.
*Color, just before opening.*—Base: RHS 145A. Apex: RHS 137A with anthocyanin.

Petals:
*Shape.*—Petal has an elliptic base and an orbicular apex.
*Quantity.*—4 per flower, imbricate.
*Petal base length.*—0.8 cm.
*Petal base width.*—0.2 cm.
*Petal base margin.*—Entire.
*Petal base texture.*—Smooth.
*Petal base color.*—Upper surface: RHS 1C. Lower surface: RHS 1C.
*Petal apex length.*—0.7 cm.
*Petal apex width.*—0.8 cm.
*Petal apex margin.*—Entire.
*Petal apex texture.*—Smooth.
*Petal apex color.*—Upper surface: RHS N78A. Lower surface: RHS N78B.

The color of the petal base is extended a little bit to the petal apex; so the flower shows a white yellow eye.

Sepals:
*Quantity.*—4 per flower.
*Shape.*—Elliptic.
*Apex.*—Acute.
*Margin.*—Entire.
*Length.*—0.8 cm.
*Width.*—0.3 cm.
*Color upper surface.*—Immature: RHS 137A with some anthocyanin. Mature: RHS 137A with very much anthocyanin.
*Color lower surface.*—RHS 138B.
*Texture upper surface.*—Smooth, pubescent.
*Texture lower surface.*—Smooth, glabrous.

Peduncles:
*Length.*—0.7 cm.
*Diameter.*—0.1 cm.
*Color.*—RHS 138A with some anthocyanin.
*Texture.*—Smooth, pubescent.

Reproductive organs:
*Androecium.*—Stamen number: 6, not fused. Filament length: 0.4–0.8 cm. Filament color: RHS 2D. Anther shape: Deltoid. Anther length: 0.2 cm. Anther color: RHS 2B. Color of pollen: RHS 2A. Amount of pollen: Normal.
*Gynoecium.*—Pistil number: One. Pistil length: 0.6 cm. Stigma color: RHS 150B. Style color: RHS N144C. Ovary color: RHS 138B.

Seed development: Seed development has not been observed.

Disease/pest resistance: No disease/pest resistance has been observed.

What is claimed is:

1. A new and distinct cultivar of *Aubrieta* plant named 'Audelmag,' as substantially illustrated and described herein.

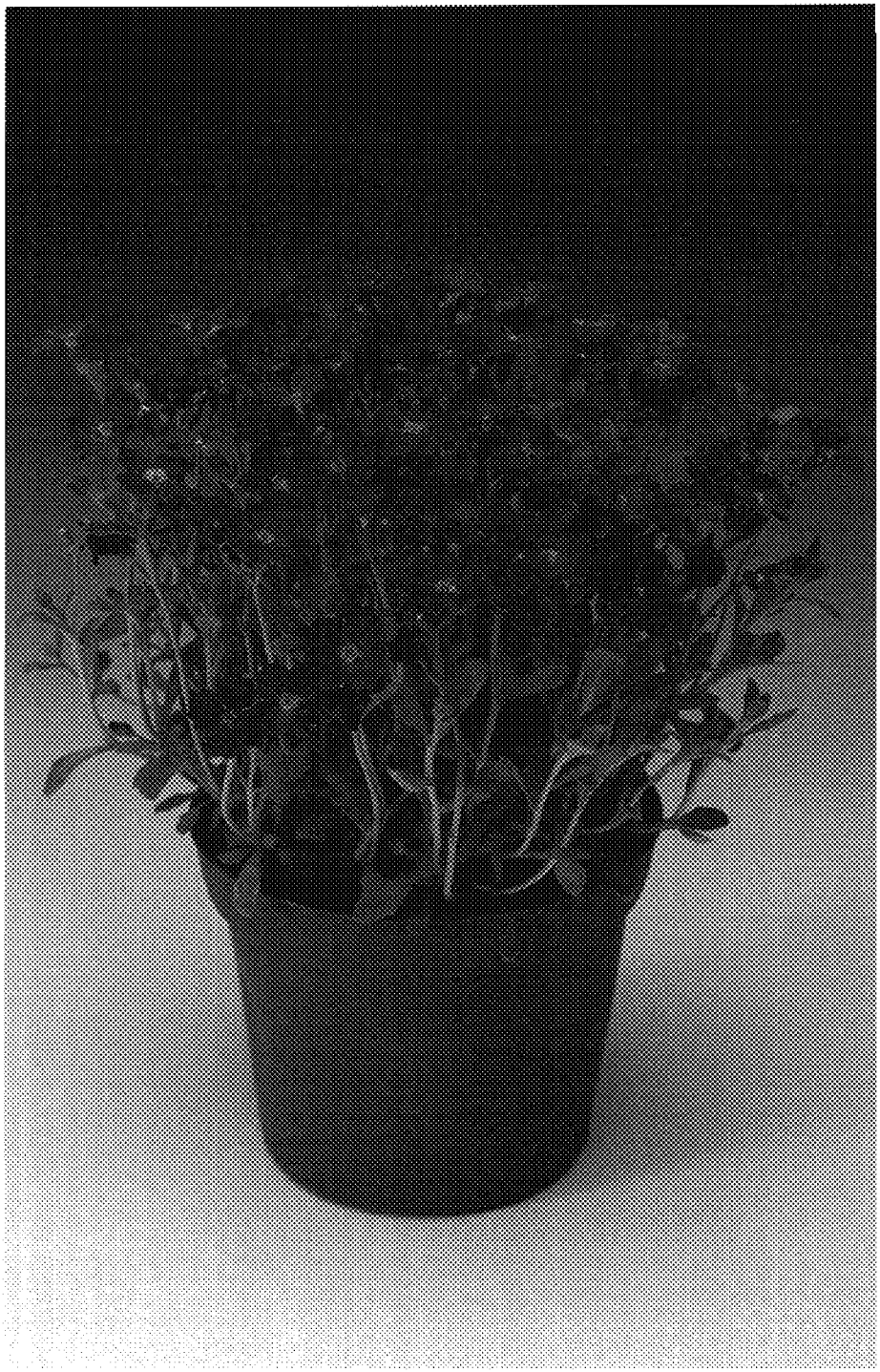

* * * * *